(12) United States Patent
Guevremont et al.

(10) Patent No.: US 6,653,627 B2
(45) Date of Patent: Nov. 25, 2003

(54) FAIMS APPARATUS AND METHOD WITH LASER-BASED IONIZATION SOURCE

(75) Inventors: Roger Guevremont, Gloucester (CX); Randy Purves, Gloucester (CX); David Barnett, Orleans (CX)

(73) Assignee: National Research Council Canada, Ottawa (CA)

( * ) Notice: Subject to any disclaimer, the term of this patent is extended or adjusted under 35 U.S.C. 154(b) by 0 days.

(21) Appl. No.: 10/220,602
(22) PCT Filed: Mar. 14, 2001
(86) PCT No.: PCT/CA01/00312
§ 371 (c)(1), (2), (4) Date: Sep. 3, 2002
(87) PCT Pub. No.: WO01/69219
PCT Pub. Date: Sep. 20, 2001

(65) Prior Publication Data
US 2003/0047681 A1 Mar. 13, 2003

Related U.S. Application Data

(60) Provisional application No. 60/189,085, filed on Mar. 14, 2000.

(51) Int. Cl.[7] ................................................. H01J 49/40
(52) U.S. Cl. ....................... 250/288; 250/281; 250/282; 250/286
(58) Field of Search ................................. 250/286, 287, 250/288, 281, 282

(56) References Cited

U.S. PATENT DOCUMENTS

| | | | | |
|---|---|---|---|---|
| 5,763,876 A | * | 6/1998 | Pertinarides et al. | ........ 250/288 |
| 6,410,914 B1 | * | 6/2002 | Park et al. | .................. 250/288 |
| 6,417,511 B1 | * | 7/2002 | Russ et al. | .................. 250/292 |

* cited by examiner

Primary Examiner—John R. Lee
Assistant Examiner—Paul M. Gurzo
(74) Attorney, Agent, or Firm—Freedman & Associates

(57) ABSTRACT

Generally, the present invention provides a device for heating the sample stream inlet of an ion mobility spectrometry (IMS) sensor. The heating device increases the temperature of the sample stream inlet surface to reduce the amount of time between adsorption and desorption taking place on the surface. This greatly improves the ability of the IMS sensor to follow rapidly changing analyte concentration levels. An alternate preferred embodiment of the present invention provides a flow smoothing device for decreasing the turbulence present in the fluid flow entering the IMS sensor's carrier stream inlet. This flow smoothing insert permits increasing the fluid flow rate entering the IMS sensor's carrier stream inlet to levels which maximize the IMS sensor's measurement sensitivity without causing mixing of the sample and carrier fluid stream flows.

22 Claims, 2 Drawing Sheets

FAIMS APPARATUS AND METHOD WITH LASER-BASED IONIZATION SOURCE

This application is the National Stage of International Application No. PCT/CA01/00312 filed Mar. 14, 2001 which claims the benefit of U.S. Provisional Application Ser. No. 60/189,085, filed Mar. 14, 2000.

FIELD OF THE INVENTION

The present invention relates to an apparatus and method for separating ions, more particularly the present invention relates to an apparatus and method for separating ions based on the ion focusing principles of high field asymmetric waveform ion mobility spectrometry (FAIMS).

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are gated into the drift tube and are subsequently separated in dependence upon differences in their drift velocity. The ion drift velocity is proportional to the electric field strength at low electric field strength, for example 200 V/cm, and the mobility, K, which is determined from experimentation, is independent of the applied electric field. Additionally, in IMS the ions travel through a bath gas that is at sufficiently high pressure such that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied field, and K becomes dependent upon the applied electric field. At high electric field strength, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry. Ions are separated in FAIMS on the basis of a difference in the mobility of an ion at high field strength, $K_h$, relative to the mobility of the ion at low field strength, K. In other words, the ions are separated because of the compound dependent behavior of $K_h$ as a function of the applied electric field strength. FAIMS offers a new tool for atmospheric pressure gas-phase ion studies since it is the change in ion mobility, and not the absolute ion mobility, that is being monitored.

The principles of operation of FAIMS using flat plate electrodes have been described by I. A. Buryakov, E. V. Krylov, E. G. Nazarov and U. Kh. Rasulev in a paper published in the International Journal of Mass Spectrometry and Ion Processes; volume 128 (1993), pp. 143–148, the contents of which are herein incorporated by reference. The mobility of a given ion under the influence of an electric field is expressed by: $K_h=K(1+f(E))$, where $K_h$ is the mobility of an ion at high electrical field strength, K is the coefficient of ion mobility at low electric field strength and f(E) describes the functional dependence of the ion mobility on the electric field strength. Ions are classified into one of three broad categories on the basis of a change in ion mobility as a function of the strength of an applied electric field, specifically: the mobility of type A ions increases with increasing electric field strength; the mobility of type C ions decreases; and, the mobility of type B ions increases initially before decreasing at yet higher field strength. The separation of ions in FAIMS is based upon these changes in mobility at high electric field strength. Consider an ion, for example a type A ion, which is being carried by a gas stream between two spaced-apart parallel plate electrodes of a FAIMS device. The space between the plates defines an analyzer region in which the separation of ions occurs. The net motion of the ion between the plates is the sum of a horizontal x-axis component due to the flowing stream of gas and a transverse y-axis component due to the electric field between the parallel plate electrodes. The term "net motion" refers to the overall translation that the ion, for instance said type A ion, experiences, even when this translational motion has a more rapid oscillation superimposed upon it. Often, a first plate is maintained at ground potential while the second plate has an asymmetric waveform, V(t), applied to it. The asymmetric waveform V(t) is composed of a repeating pattern including a high voltage component, $V_1$, lasting for a short period of time $t_2$ and a lower voltage component, $V_2$, of opposite polarity, lasting a longer period of time $t_1$. The waveform is synthesized such that the integrated voltage-time product, and thus the field-time product, applied to the plate during each complete cycle of the waveform is zero, for instance $V_1t_2+V_2t_1=0$; for example +2000 V for 10 µs followed by −1000 V for 20 µs. The peak voltage during the shorter, high voltage portion of the waveform is called the "dispersion voltage" or DV in this disclosure.

During the high voltage portion of the waveform, the electric field causes the ion to move with a transverse y-axis velocity component $v_1=K_hE_{high}$, where $E_{high}$ is the applied field, and $K_h$ is the high field ion mobility under ambient electric field, pressure and temperature conditions. The distance traveled is $d_1=v_1t_2=K_hE_{high}t_2$, where $t_2$ is the time period of the applied high voltage. During the longer duration, opposite polarity, low voltage portion of the asymmetric waveform, the y-axis velocity component of the ion is $v_2=KE_{low}$, where K is the low field ion mobility under ambient pressure and temperature conditions. The distance traveled is $d_2=v_2t_1=KE_{low}t_1$. Since the asymmetric waveform ensures that $(V_1t_2)+(V_2t_1)=0$, the field-time products $E_{high}t_2$ and $E_{low}t_1$ are equal in magnitude. Thus, if $K_h$ and K are identical, $d_1$ and $d_2$ are equal, and the ion is returned to its original position along the y-axis during the negative cycle of the waveform, as would be expected if both portions of the waveform were low voltage. If at $E_{high}$ the mobility $K_h>K$, the ion experiences a net-displacement from its original position relative to the y-axis. For example, positive ions of type A travel farther during the positive portion of the waveform, for instance $d_1>d_2$, and the type A ion migrates away from the second plate. Similarly, positive ions of type C migrate towards the second plate.

If a positive ion of type A is migrating away from the second plate, a constant negative dc voltage can be applied to the second plate to reverse, or to "compensate" for, this transverse drift. This dc voltage, called the "compensation voltage" or CV in this disclosure, prevents the ion from migrating towards either the second or the first plate. If ions derived from two compounds respond differently to the applied high strength electric fields, the ratio of $K_h$ to K may be different for each compound. Consequently, the magnitude of the CV necessary to prevent the drift of the ion toward either plate is also different for each compound. Thus, when a mixture including several species of ions is being analyzed by FAIMS, only one species of ion is selectively transmitted for a given combination of CV and DV. The remaining species of ions, for instance those ions that are other than selectively transmitted through FAIMS, drift towards one of the parallel plate electrodes of FAIMS and are neutralized. Of course, the speed at which the remaining species of ions move towards the electrodes of FAIMS depends upon the degree to which their high field mobility properties differ from those of the ions that are selectively transmitted under the prevailing conditions of CV and DV.

An instrument operating according to the FAIMS principle as described previously is an ion filter, capable of selective transmission of only those ions with the appropriate ratio of $K_h$ to K. In one type of experiment using FAIMS devices, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained. It is a significant limitation of early FAIMS devices, which used electrometer detectors, that the identity of peaks appearing in the CV spectrum are other than unambiguously confirmed solely on the basis of the CV of transmission of a species of ion. This limitation is due to the unpredictable, compound-specific dependence of $K_h$ on the electric-field strength. In other words, a peak in the CV spectrum is easily assigned to a compound erroneously, since there is no way to predict or even to estimate in advance, for example from the structure of an ion, where that ion should appear in a CV spectrum. In other words, additional information is necessary in order to improve the likelihood of assigning correctly each of the peaks in the CV spectrum. For example, subsequent mass spectrometric analysis of the selectively transmitted ions greatly improves the accuracy of peak assignments of the CV spectrum.

In U.S. Pat. No. 5,420,424 which issued on May 30, 1995, B. L. Carnahan and A. S. Tarassove disclose an improved FAIMS electrode geometry in which the flat plates that are used to separate the ions are replaced with concentric cylinders, the contents of which are herein incorporated by reference. The concentric cylinder design has several advantages, including higher sensitivity compared to the flat plate configuration, as was discussed by R. W. Purves, R. Guevremont, S. Day, C. W. Pipich, and M. S. Matyjaszczyk in a paper published in Reviews of Scientific Instruments; volume 69 (1998), pp 4094–4105. The higher sensitivity of the cylindrical FAIMS is due to a two-dimensional atmospheric pressure ion focusing effect that occurs in the analyzer region between the concentric cylindrical electrodes. When no electrical voltages are applied to the cylinders, the radial distribution of ions should be approximately uniform across the FAIMS analyzer. During application of DV and CV, however, the radial distribution of ions is not uniform across the annular space of the FAIMS analyzer region. Advantageously, with the application of an appropriate DV and CV for an ion of interest, those ions become focused into a band between the electrodes and the rate of loss of ions, as a result of collisions with the FAIMS electrodes, is reduced. The efficiency of transmission of the ions of interest through the analyzer region of FAIMS is thereby improved as a result of this two-dimensional ion focusing effect.

The focussing of ions by the use of asymmetric waveforms has been discussed above. For completeness, the behavior of those ions that are not focussed within the analyzer region of a cylindrical geometry PAIMS is described here, briefly. As discussed previously, those ions having high field ion mobility properties that are other than suitable for focussing under a given set of DV, CV and geometric conditions will drift toward one or another wall of the PAIMS device. The rapidity with which these ions move towards the wall depends on the degree to which their $K_h/K$ ratio differs from that of the ion that is transmitted selectively under the prevailing conditions. At the very extreme, ions of completely the wrong property, for instance a type A ion versus a type C ion, are lost to the walls of the FAIMS device very rapidly.

The loss of ions in FAIMS devices should be considered one more way. If an ion of type A is focussed, for example at DV 2500 volts, CV −11 volts in a given geometry, it would seem reasonable to expect that the ion is also focussed if the polarity of DV and CV are reversed, for instance DV of −2500 volts and CV of +11 volts. This, however, is not observed and in fact the reversal of polarity in this manner creates a mirror image effect of the ion-focussing behavior of FAIMS. The result of such polarity reversal is that the ions are not focussed, but rather are extremely rapidly rejected from the device. The mirror image of a focussing valley, is a hill-shaped potential surface. The ions slide to the center of the bottom of a focussing potential valley (2 or 3-dimensions), but slide off of the top of a hill-shaped surface, and hit the wall of an electrode. This is the reason for the existence, in the cylindrical geometry FAIMS, of the independent "modes" called 1 and 2. Such a FAIMS instrument is operated in one of four possible modes: P1, P2, N1, and N2. The "P" and "N" describe the ion polarity, positive (P) and negative (N). The waveform with positive DV, where DV describes the peak voltage of the high voltage portion of the asymmetric waveform, yields spectra of type P1 and N2, whereas the reversed polarity negative DV, waveform yields P2 and N1. The discussion thus far has considered positive ions but, in general, the same principles apply to negative ions equally.

A further improvement to the cylindrical FAIMS design is realized by providing a curved surface terminus of the inner electrode. The curved surface terminus is continuous with the cylindrical shape of the inner electrode and is aligned co-axially with an ion-outlet orifice of the FAIMS analyzer region. The application of an asymmetric waveform to the inner electrode results in the normal ion-focussing behavior described above, except that the ion-focussing action extends around the generally spherically shaped terminus of the inner electrode. This means that the selectively transmitted ions cannot escape from the region around the terminus of the inner electrode. This only occurs if the voltages applied to the inner electrode are the appropriate combination of CV and DV as described in the discussion above relating to 2-dimensional focussing. If the CV and DV are suitable for the focussing of an ion in the FAIMS analyzer region, and the physical geometry of the inner surface of the outer electrode does not disturb this balance, the ions will collect within a three-dimensional region of space near the terminus. Several contradictory forces are acting on the ions in this region near the terminus of the inner electrode. The force of the carrier gas flow tends to influence the ion cloud to travel towards the ion-outlet orifice, which advantageously also prevents the trapped ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focussing effect of the electric fields of the FAIMS mechanism. This is an example of a three-dimensional atmospheric pressure ion trap, as disclosed in a copending PCT application in the name of R. Guevremont and R. Purves, the contents of which are herein incorporated by reference.

Ion focusing and ion trapping requires electric fields that are other than constant in space, normally occurring in a geometrical configuration of FAIMS in which the electrodes are curved, and/or are not parallel to each other. For example, a non-constant in space electric field is created using electrodes that are cylinders or a part thereof; electrodes that are spheres or a part thereof; electrodes that are elliptical spheres or a part thereof; and, electrodes that are conical or a part thereof. Optionally, various combinations of these electrode shapes are used.

As discussed above, one previous limitation of the cylindrical FAIMS technology is that the identity of the peaks appearing in the CV spectra are not unambiguously confirmed due to the unpredictable changes in $K_h$ at high electric field strengths. Thus, one way to extend the capability of instruments based on the FAIMS concept is to provide a way to determine the make-up of the CV spectra more accurately, such as by introducing ions from the FAIMS device into a mass spectrometer for mass-to-charge (m/z) analysis. Advantageously, the ion focusing property of cylindrical FAIMS devices acts to enhance the efficiency for transporting ions from the analyzer region of a FAIMS device into an external sampling orifice, for instance an inlet of a mass spectrometer. This improved efficiency of transporting ions into the inlet of the mass spectrometer is optionally maximized by using a 3-dimensional trapping version of FAIMS operated in nearly trapping conditions. Under near-trapping conditions, the ions that have accumulated in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a small orifice leading into the vacuum system of a mass spectrometer.

Additionally, the resolution of a FAIMS device is defined in terms of the extent to which ions having similar mobility properties as a function of electric field strength are separated under a set of predetermined operating conditions. Thus, a high-resolution FAIMS device transmits selectively a relatively small range of different ion species having similar mobility properties, whereas a low-resolution FAIMS device transmits selectively a relatively large range of different ion species having similar mobility properties. The resolution of FAIMS in a cylindrical geometry FAIMS is compromised relative to the resolution in a parallel plate geometry FAIMS because the cylindrical geometry FAIMS has the capability of focusing ions. This focusing action means that ions of a wider range of mobility characteristics are simultaneously focused in the analyzer region of the cylindrical geometry FAIMS. A cylindrical geometry FAIMS with narrow electrodes has the strongest focusing action, but the lowest resolution for separation of ions. As the radii of curvature are increased, the focusing action becomes weaker, and the ability of FAIMS to simultaneously focus ions of similar high-field mobility characteristics is similarly decreased. This means that the resolution of FAIMS increases as the radii of the electrodes are increased, with parallel plate geometry FAIMS having the maximum attainable resolution.

Note that, while the above discussion refers to the ions as being "captured" or "trapped", in fact, the ions are subject to continuous 'diffusion'. Diffusion always acts contrary to focussing and trapping. The ions always require an electrical, or gas flow force to reverse the process of diffusion. Thus, although the ions are focused into an imaginary cylindrical zone in space with almost zero thickness, or within a 3-dimensional ion trap, in reality it is well known that the ions are actually dispersed in the vicinity of this idealized zone in space because of diffusion. This is important, and should be recognized as a global feature superimposed upon all of the ion motions discussed in this disclosure. This means that, for example, a 3-dimensional ion trap actually has real spatial width, and ions continuously leak from the 3-dimensional ion trap, for several physical, and chemical reasons. Of course, the ions occupy a smaller physical region of space if the trapping potential well is deeper.

It is a limitation of the prior art FAIMS devices that ions are typically introduced into FAIMS after being formed by one of several versions of atmospheric pressure ionization, including corona discharge ionization, ionization by radioactive Ni, and electrospray ionization. In every case the sample is one of a liquid and a gas, and in every case the analyte ions are suspended in a gas. Of course, these ionization sources are adaptable for use with FAIMS with relatively slight or no changes to the FAIMS device itself. Further, each of these ionization sources must be operated external to the FAIMS analyzer region and the ions so produced swept into the analyzer region using a carrier gas. This involves a transport process which can lower ion transmission and therefore reduces operating efficiency.

It would be advantageous to provide a method and an apparatus for introducing analyte ions from compounds, which are other than amendable to the above listed ionization techniques, into the analyzer of FAIMS. Advantageously, different species of ions, in particular large biological molecules such as full scale proteins, could be analyzed routinely using a FAIMS device that is operationally interfaced to a suitable ionization source. This would extend the usefulness of FAIMS to include other disciplines for which the current ionization techniques are other than appropriate.

OBJECT OF THE INVENTION

In order to overcome these and other limitations of the prior art, it is an object of the present invention to provide a high field ion mobility spectrometer for separating ions in which the ions are produced from an ion source within the analyzer region under approximately standard temperature and pressure conditions.

In order to overcome these and other limitations of the prior art, it is an object of the present invention to provide a high field ion mobility spectrometer for separating ions in which ions are produced using a laser based ionization technique operating under approximately standard temperature and pressure conditions.

SUMMARY OF THE INVENTION

In accordance with the invention there is provided a method for selectively transmitting ions produced by a laser-based ionization technique, comprising the steps of:

a) providing two electrodes including a first electrode and a second electrode;

b) providing an asymmetric waveform and a direct-current compensation voltage, to at least one of the two electrodes to form an electric field therebetween, the field for effecting a difference in net displacement between ions in a time of one cycle of the applied asymmetric waveform for effecting a first separation of the ions by forming a subset thereof;

c) producing ions within the electric field using a laser-based ionization technique; and, d) transporting said produced ions through the electric field in a direction approximately transverse to the electric field, wherein the ions are produced under other than high vacuum conditions.

In accordance with the invention there is provided an apparatus for selectively transmitting ions produced by a laser-based ionization technique, including:

a source of laser light for providing laser light for ionizing a sample;

a FAIMS analyzer comprising:

two electrodes disposed for allowing at least a gas to pass therebetween and for providing an electric field therebetween resulting from an application of an asymmetric waveform to at least one of the electrodes in order to affect ion mobility; and, at least a light transmissive port for providing laser light received from the source of laser light to irradiate a sample within the analyzer region in order to ionize the sample.

In accordance with the invention there is provided an apparatus for selectively transmitting ions produced by a laser-based ionization technique, including:

a FAIMS analyzer comprising:

two electrodes, for providing an electric field therebetween resulting from an application of an asymmetric waveform to at least one of the electrodes in order to affect ion mobility, and for allowing at least a gas to pass therebetween;

at least a light transmissive port for receiving laser light; and, a surface for receiving an ion source, the surface in optical communication with the at least a light transmissive port, such that, in use, laser light received through the port and impinging upon the ion source causes ionization thereof.

In accordance with the invention there is provided an apparatus for selectively transmitting ions produced by a laser-based ionization technique, including:

a FAIMS analyzer comprising:

two electrodes, for providing an electric field therebetween resulting from an application of an asymmetric waveform to at least one of the electrodes in order to affect ion mobility, and for allowing at least a gas to pass therebetween;

at least a light transmissive port for receiving laser light; and, a surface for receiving a substrate having a sample on a surface thereof, the surface in optical communication with the at least a light transmissive port, such that, in use, laser light received through the port and impinging upon the sample causes ionization thereof.

DETAILED DESCRIPTION OF THE INVENTION

Figure 1:
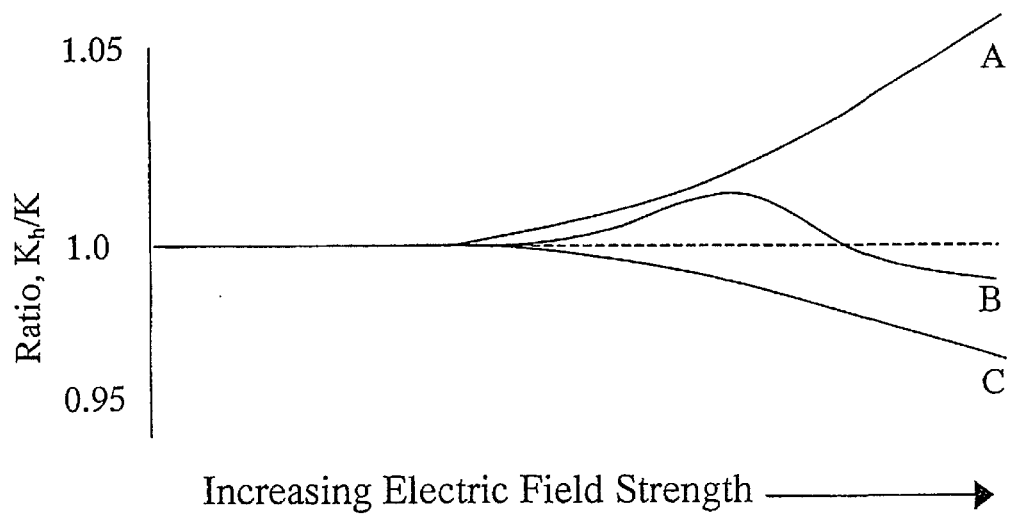
FIG. 1 shows three possible examples of changes in ion mobility as a function of the strength of an electric field.

Referring to FIG. 1, shown are three possible examples of the change in ion mobility properties with increasing electric field strength, as was discussed previously. The separation of ions in FAIMS is based upon a difference in these mobility properties for a first ion relative to a second ion. For instance, a first type A ion having a low field mobility $K_{1,low}$ is not separated in a FAIMS device from a second type A ion having a second different low field mobility $K_{2,low}$, if under the influence of high electric field strength, the ratio $K_{1,high}/K_{1,low}$ is equal to the ratio $K_{2,high}/K_{2,low}$. Interestingly, however, this same separation is achieved using conventional ion mobility spectrometry, which is based on a difference in ion mobilities at low applied electric field strength.

Figure 2A:
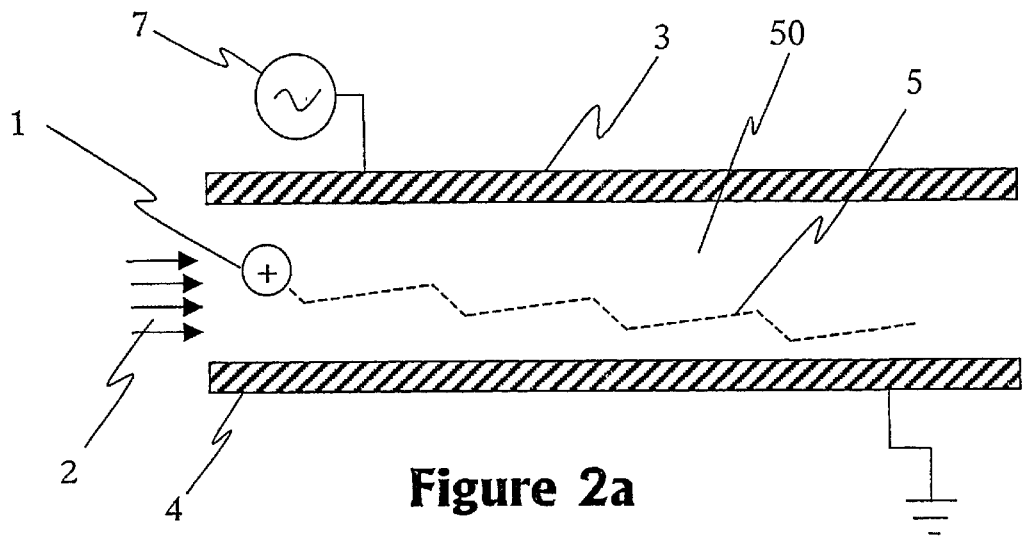
FIG. 2a illustrates the trajectory of an ion between two parallel plate electrodes under the influence of the electrical potential V(t)
Figure 2B:
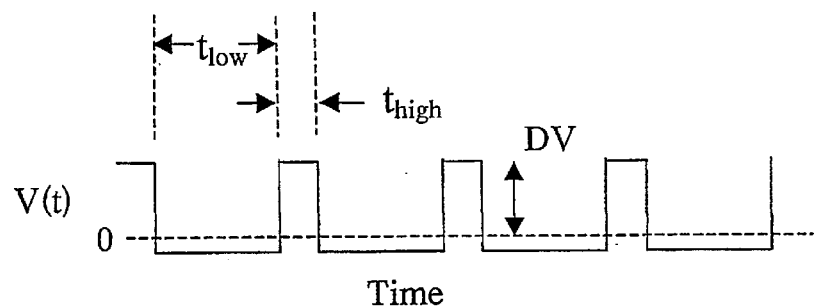
FIG. 2b shows an asymmetric waveform described by V(t)

Referring to FIG. 2a, shown is a schematic diagram illustrating the mechanism of ion separation according to the FAIMS principle. An ion 1, for instance a positively charged type A ion, is carried by a gas stream 2 flowing between two spaced apart parallel plate electrodes 3 and 4. One of the plates 4 is maintained at ground potential, while the other plate 3 has an asymmetric waveform described by V(t), applied to it. The peak voltage applied during the waveform is called the dispersion voltage (DV), as is shown in FIG. 2b. Referring still to FIG. 2b, the waveform is synthesized so that the electric fields during the two periods of time $t_{high}$ and $t_{low}$ are not equal. If $K_h$ and K are identical at high and low fields, the ion 1 is returned to its original position at the end of one cycle of the waveform. However, under conditions of sufficiently high electric fields, $K_h$ is greater than K and the distances traveled during $t_{high}$ and $t_{low}$ are no longer identical. Within an analyzer region defined by a space 50 between the first and second spaced apart electrode plates, 3 and 4, respectively, the ion 1 experiences a net displacement from its original position relative to the plates 3 and 4, as illustrated by the dashed line 5 in FIG. 2a.

If a type A ion is migrating away from the upper plate 3, a constant negative dc compensation voltage CV is applied to plate 3 to reverse or "compensate" for this offset drift. Thus, the ion 1 does not travel toward either plate. If two species of ions respond differently to the applied high electric field, for instance the ratios of $K_h$ to K are not identical, the compensation voltages necessary to prevent their drift toward either plate are similarly different. To analyze a mixture of ions, the compensation voltage is, for example, scanned to transmit each of the components of a mixture in turn. This produces a compensation voltage spectrum, or CV spectrum.

It is well known that ions are formed from samples, under certain conditions, by the use of a high power laser beam. One important analytical technique called matrix-assisted laser desorption ionization (MALDI), is based on this concept. In a MALDI experiment one of a solid and a liquid sample is mixed with a material called a 'matrix', and this sample/matrix combination is dried onto a metal support electrode. A laser beam is directed onto this surface, and ions of the analyte compound are formed. The composition of this 'matrix' is critical, in fact crucially important to the success of this method. The ions cannot be formed efficiently in the absence of the appropriate-matrix. Further, often it is necessary to irradiate a sample/matrix spot in several places to find a 'hot spot' that results in ion formation.

It will be obvious to one of skill in the art that existing FAIMS apparatus are other than compatible for interfacing directly to a MALDI source. For instance, MALDI is typically performed in a vacuum chamber. This is because MALDI is a non-specific ionization technique, such that a plume including both positively and negatively charged ion species, is produced above the sample spot. Of course, there is a natural tendency for ions of opposite charge to re-combine, therefore, unless the dense plume of ions is rapidly dissipated, for instance within a low pressure vacuum chamber, some of the ions of interest are lost very quickly. Additionally, it is typically other than convenient to introduce the sample/matrix mixture into a prior art FAIMS apparatus. Further additionally, FAIMS apparatus according to the prior art do not allow for irradiation of a sample within the analyzer region.

Figure 3:
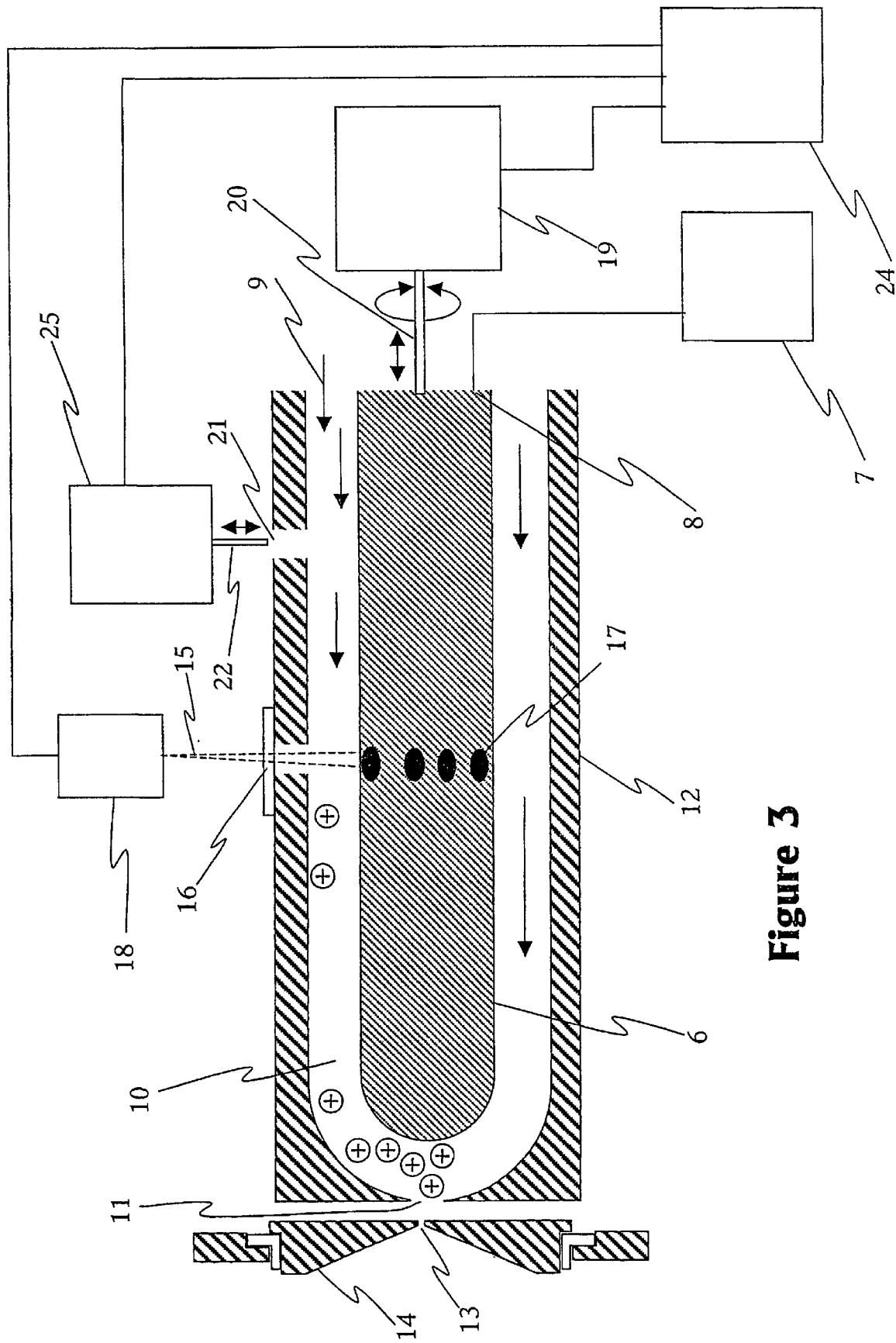
FIG. 3 shows a FAIMS device with a laser-based ionization source according to a preferred embodiment of the present invention.

Referring to FIG. 3, shown is a simplified block diagram of a FAIMS device with a laser-based ionization source (maldiFAIMS) according to a preferred embodiment of the present invention. The laser-based ionization source is a matrix-assisted laser desorption ionization (MALDI) source. The FAIMS comprises an inner FAIMS electrode 6 to which a high voltage asymmetric waveform and a low voltage dc compensation voltage are applied by power supply 7, through electrical contact 8. The inner electrode 6 is mounted in an electrically insulating block (not shown). The gas 9 serves as the carrier gas in the analyzer region 10. The gas exits the analyzer region through orifice 11 in the outer electrode 12, and enters a mass spectrometer (not shown) through an orifice 13 in the orifice plate 14. The ions which pass through the orifice 13 in said plate 14, travel to a skimmer cone (not shown) in the differentially pumped region of the mass spectrometer (not shown). Alternatively, a different detection means, such as an electrometric ion detector, is provided in place of the mass spectrometer.

Still referring to FIG. 3, the ions are formed by the impact of a laser beam 15 that passes through a window 16 in the FAIMS outer electrode 12 and strikes the sample spot 17 that is deposited on the surface of the FAIMS inner electrode 6. The laser beam 15 is generated by a laser beam source 18.

In use, the samples are deposited on the FAIMS inner electrode 6 while the electrode is withdrawn from its operating location, for instance using a motorized translational device 19. The motorized translational device 19 is connected to the inner electrode 6 through an insulating rod 20. The motorized translational device 19 is capable of longitudinal translation of the inner electrode 6, and it is also capable of rotation of the inner electrode 6. The samples and appropriate matrix are applied as a series of spots 17 arranged around the circumference of the inner FAIMS electrode 6. The sample spots 17 are optionally dried in an apparatus separately from the system shown in FIG. 3, however in the system shown in FIG. 3 the samples are applied to the inner electrode 6 through a sample introduction port 21. A mechanical sample applicator 22 delivers the sample to the surface of the inner electrode 6 such that spots 17 are located substantially adjacent to the sample introduction port 21. The solvent vapor that results from the drying of the spots 17 is carried partly out of the FAIMS device through port 21.

Still referring to FIG. 3, when the samples have been prepared, the inner electrode 6 of maldiFAIMS is re-inserted using the motorized translational device 19. The portion of gas flow 9 which does not escape through sample introduction port 21 acts to purge the FAIMS analyzer region 10, and to carry the ions along the length of the analyzer region 10. The laser 18 is activated for each sample spot 17 for the appropriate number of pulses to induce ionization of the sample molecules. The inner electrode 6 is rotated using the connection 20, such that each sample 17 is brought in turn into the beam of the laser. The inner electrode 6 is rotated very slowly while the beam impinges on each sample in order to maximize the amount of new sample material that is available to the laser beam 15.

The location and position of the inner electrode 6 inside of the FAIMS outer electrode 12 is very critical, especially the location of the spherical domed terminus 23 of the inner electrode 6. This position must be accurately controlled using the motorized translational device 19. All aspect of the timing of the movements of the inner electrode 6, delivery of sample droplets to spots 17, and ionization of the samples with laser beam 15, are controlled by computer system 24, which delivers the electronic signals to the motorized translational device 19, to the sample introduction unit 25, and the laser power supply 18.

Of course, often the pressure that is maintained within the FAIMS analyzer region is approximately one standard atmosphere. For instance, ion focusing within the FAIMS analyzer region is a consequence of collisions, occurring in the gas phase, between the analyte ions and the neutral molecules of the carrier, or bath, gas. Absent said bath gas, the ions continue to accelerate under the influence of the applied electric field, and separation is other than achieved. Of course, FAIMS devices are optionally operated at reduced pressure, however, in such cases the applied electric field strength is decreased as the number density of the bath gas is decreased. Further, even the minimum effective operating pressures for the FAIMS device are several orders of magnitude higher than the pressures required for effective ion production with a MALDI source. As will be obvious to one of skill in the art, the plume of ions produced above the sample/matrix mixture encounter molecules of the dense bath gas, suffering repeated collisions therewith, which collectively impede the rapid dispersion of the ions. The ions, being forced to occupy a small three-dimensional region of space, tend to collide with other ions and re-combine.

It is an unexpected advantage of FAIMS, however, that the applied strong electric fields influence the trajectories of the produced ions, such that the ions are captured by the focusing action of FAIMS and removed from the ionization zone as they are produced. Triggering of the laser pulse to coincide with the beginning of the high voltage portion of the asymmetric waveform, which tends to cause the ions of interest to move away from the inner electrode. Thus, the plume of ions that is generated by the MALDI source is effectively dispersed very rapidly, even under conditions of relatively high operating pressure, by the action of the applied strong electric fields. Further advantageously, those ions having other than appropriate high field mobility properties to be selectively transmitted through the analyzer region migrate towards one of the FAIMS electrodes and are lost. Since MALDI produces a huge plume of ions at virtually every mass-to-charge (m/z) ratio, it is highly advantageous that FAIMS rapidly separates the analyte ions from the ions that are other than of interest. Since the ion losses occurring immediately after ionization are minimized, the sensitivity of maldiFAIMS is increased and detection limits for analyte ions are similarly improved.

The maldiFAIMS is optionally operated by removing completely the inner electrode 6 for application of the sample. A series of exchangeable inner electrodes 6 are further optionally substituted for each other during the course of the analysis of a series of samples. Whereas in the present embodiment the inner electrode 6 is moved to present new sample spots 17 to the laser beam 15, it is optionally possible for the laser beam 15 to be directed in sequence to a series of different sample spots 17 located on the inner electrode 6. Sample spots are optionally placed on the outer electrode 12. Sample spots are further optionally placed on a transparent window similar to transparent window 16 shown in FIG. 3, which is mounted onto the outer electrode of FAIMS with the sample spot facing inwards to the analyzer region 10 of FAIMS. The laser beam 15 therefore passes through the transparent window material and strikes the sample. The ions formed from this surface are then captured by the focusing action of FAIMS as discussed previously, and separated by FAIMS within analyzer region 10.

Further alternatively, a FAIMS device having other than cylindrical geometry is interfaced to the laser-based ionization source. For instance, FAIMS devices having three or more electrodes, wherein the electrodes are one of flat parallel plates and curved plates, are disclosed by the present inventors in a related PCT application entitled FAIMS Improvements. Modifications similar to those described with reference to FIG. 3 for the cylindrical electrode geometry FAIMS, for example to permit sample introduction and sample irradiation, are also easily envisioned for the alternate geometry FAIMS devices.

Of course, numerous other embodiments could be envisioned, without departing significantly from the teachings of the present invention.

What is claimed is:

1. A method for selectively transmitting ions produced by a laser-based ionization technique, comprising the steps of:
    a) providing two electrodes including a first electrode and a second electrode defining a FAIMS analyzer therebetween;
    b) providing an asymmetric waveform and a direct-current compensation voltage, to at least one of the two electrodes to form an electric field therebetween, the field for effecting a difference in net displacement between ions in a time of one cycle of the applied asymmetric waveform for effecting a first separation of the ions by forming a subset thereof;
    c) producing ions within the electric field using a laser-based ionization technique; and,
    d) transporting said produced ions through the electric field in a direction approximately transverse to the electric field,
wherein the ions are produced under other than high vacuum conditions.

2. A method according to claim 1, wherein the step of transporting includes the step of: providing a flow of a carrier gas for transporting said produced ions through the electric field in a direction transverse to the electric field.

3. A method according to claim 2, including the additional steps prior to step b) of:
    a2) applying at least a spot of an analyte species to a surface within an irradiation zone on one of the two electrodes, the surface facing inwardly toward the analyzer region.

4. A method according to claim 2, including the step of detecting said selectively transmitted ions by mass spectrometry.

5. A method according to claim 3, including the additional steps prior to step a2) of:
    a1) mixing a sample including the analyte species with an appropriate matrix material before application thereof.

6. A method according to claim 3, including the additional steps prior to step a2) of:
    a1) applying an appropriate matrix material to the surface.

7. A method according to claim 3, wherein the spot is applied onto a surface of one of the first and second electrodes.

8. A method according to claim 3, wherein the spot is applied onto a surface of a transparent window that is mounted onto one of the first and second electrodes.

9. A method according to claim 3, wherein the step c includes steps of:
    c1) irradiating a first region of the surface to which the at least a spot is applied with a pulse of laser light; and,
    c2) moving the surface to which the at least a spot is applied relative to the incident laser light, to irradiated a second different region of the surface that is other than irradiated in step (c1).

10. A method according to claim 9, including the step of timing the irradiation by a pulse of laser light to coincide with a high voltage portion of the asymmetric waveform to cause the produced ions of interest to move away from one of the two electrodes in the time of the high voltage portion of at least a cycle of the applied asymmetric waveform.

11. A method according to claim 9, wherein step b2) includes the additional steps of:
    i) relatively moving the first electrode and the second electrode to position the irradiation zone for receiving the spot of the mixture including the analyte species; and,
    ii) relatively moving the first electrode and the second electrode to position the irradiation zone, having the spot of the mixture including the analyte species thereon, for irradiation by the laser light.

12. An apparatus for selectively transmitting ions produced by a laser-based ionization technique, including:
    a source of laser light for providing laser light for ionizing a sample;
    a FAIMS analyzer comprising:
        two electrodes disposed for allowing at least a gas to pass therebetween and for providing an electric field therebetween resulting from an application of an asymmetric waveform to at least one of the electrodes in order to affect ion mobility; and,
        at least a light transmissive port for providing laser light received from the source of laser light to irradiate a sample within the analyzer region in order to ionize the sample.

13. An apparatus according to claim 12, wherein the two electrodes include one each of an inner and an outer cylindrical electrode in substantially overlapping coaxial alignment.

14. An apparatus according to claim 13, comprising an actuator for relatively moving the inner and outer electrodes.

15. An apparatus according to claim 14, wherein the actuator is for relatively moving the inner electrode with a translational motion from a first position to a second position for receiving a sample from a sample applicator and from the a second position to the first position.

16. An apparatus according to claim 15, wherein the actuator is for relatively moving the inner electrode with a rotational motion for applying the sample around the circumference of the inner electrode when the electrode is in the second position.

17. An apparatus according to claim 16, wherein the actuator is for relatively moving the inner electrode with a rotational motion for irradiating the sample, the sample applied around the circumference of the inner electrode.

18. An apparatus for selectively transmitting ions produced by a laser-based ionization technique, including:
 a FAIMS analyzer comprising:
  two electrodes, for providing an electric field therebetween resulting from an application of an asymmetric waveform to at least one of the electrodes in order to affect ion mobility, and for allowing at least a gas to pass therebetween;
  at least a light transmissive port for receiving laser light; and,
  a surface for receiving an ion source, the surface in optical communication with the at least a light transmissive port, such that, in use, laser light received through the port and impinging upon the ion source causes ionization thereof.

19. An apparatus according to claim 18, comprising a source of laser light in optical communication with the at least a light transmissive port, for providing laser light to the at least a light transmissive port.

20. An apparatus according to claim 19, comprising at least a gas inlet and a gas outlet for introducing a flow of the at least a gas through the analyzer region and out of the gas outlet.

21. An apparatus according to claim 20, comprising a third electrode, the third electrode disposed between the first and the second electrode in a spaced apart stacked arrangement for providing an electric field therebetween resulting from an application of an asymmetric waveform to at least one of the electrodes, and for allowing ion flow therebetween, wherein, in use, ions exiting from between the electrodes are other than attracted to the third electrode to collide therewith.

22. An apparatus for selectively transmitting ions produced by a laser-based ionization technique, including:
 a FAIMS analyzer comprising:
  two electrodes, for providing an electric field therebetween resulting from an application of an asymmetric waveform to at least one of the electrodes in order to affect ion mobility, and for allowing at least a gas to pass therebetween;
  at least a light transmissive port for receiving laser light; and,
  a surface for receiving a substrate having a sample on a surface thereof, the surface in optical communication with the at least a light transmissive port, such that, in use, laser light received through the port and impinging upon the sample causes ionization thereof.

* * * * *

UNITED STATES PATENT AND TRADEMARK OFFICE
CERTIFICATE OF CORRECTION

PATENT NO. : 6,653,627 B2
DATED : November 25, 2003
INVENTOR(S) : Guevremont, Purves and Barnett It is certified that error appears in the above-identified patent and that said Letters Patent is hereby corrected as shown below:

<u>Title page,</u>
Item [75], Inventors, should read: -- Roger Guevremont, Gloucester (CA); Randy Purves, Gloucester (CA); David Barnett, Orleans (CA) --

Item [57], ABSTRACT, should read: -- A method and an apparatus for selectively transmitting ions produced by a laser-based ionization technique is disclosed. The method relies on a FAIMS analyzer having a surface disposed therein for receiving a sample on the surface. The surface is in optical communication with a light transmissive port through which the laser light is directed such that it impinges upon the sample and causes ionization thereof".

<u>Column 12,</u>
Lines 7-8, "the analyzer region" should read -- an analyzer region --.
Line 30, "to irradiated" should read -- to irradiate --.

<u>Column 13,</u>
Lines 6-7, "the a second" should read -- the second --.

Signed and Sealed this

Fourth Day of May, 2004

JON W. DUDAS
*Acting Director of the United States Patent and Trademark Office*